United States Patent [19]

Elliott

[11] Patent Number: 4,634,797

[45] Date of Patent: Jan. 6, 1987

[54] COUPLING OF CHLOROPERFLUOROALKANES

[75] Inventor: Arthur J. Elliott, Sloatsburg, N.Y.

[73] Assignee: Halocarbon Products Corporation, Hackensack, N.J.

[21] Appl. No.: 698,989

[22] Filed: Feb. 7, 1985

[51] Int. Cl.⁴ .............................................. C07C 17/26
[52] U.S. Cl. .................................................... 570/171
[58] Field of Search ......................................... 570/171

[56] References Cited

U.S. PATENT DOCUMENTS 2,694,701 11/1954 Blum et al. ........................... 570/139
2,705,229 3/1955 Ruh et al. ............................. 570/138
3,046,304 7/1962 Haszeldine ........................... 570/171
3,317,618 5/1967 Haszeldine ........................... 570/134

*Primary Examiner*—Natalie Trousof
*Assistant Examiner*—Joseph A. Boska
*Attorney, Agent, or Firm*—Sprung Horn Kramer & Woods

[57] ABSTRACT

A process for the coupling of a chloroperfluoroalkane having a —CFCl$_2$ moiety which comprises heating the alkane at a temperature of about 150° to 260° C. in the presence of at least about 0.1 times the molar amount each of copper and zinc at a mole ratio of copper:zinc from about 2:1 to 1:2. The product is obtained in relatively high yield and conversion.

9 Claims, No Drawings

COUPLING OF CHLOROPERFLUOROALKANES

The present invention relates to a process for coupling of chloroperfluorocarbons and the like, obtained in the telomerization of chlorotrifluoroethylene.

Chloroperfluorocarbon telomer oils, that is alkanes containing only chlorine and fluorine substituents, have the classical formula Cl(CF$_2$CFCl)$_n$Cl, where n ranges from 2 to about 7, although isomers and related compounds varying slightly in the chlorine content are produced in the manufacturing process. These telomers have excellent chemical and heat stability and thus are suitable as lubricants, hydraulic fluids, instrument fluids, etc., even under severe conditions which cause hydrocarbon oils to deteriorate rapidly. Sometimes, however, the heavier oils are needed, and a method of coupling the lighter oils would be desirable.

While metal-promoted coupling of polyfluoroiodides and bromides is well known (Chemistry of Organic Fluorine Compounds, M. Hudlicky, Ellis Horwood Ltd., New York, p. 400 (1976)), there are few examples of analogous coupling of alkyl chlorides. Radziszewski (Berichte, Vol. 17, p. 834 (1884)) reported that the reaction of copper with carbon tetrachloride at elevated temperature gave hexachloroethane as follows:

  (1)

The corresponding coupling of trichlorides such as benzotrichloride has been reported to give low yields of 1,2-diaryltetrachloroethanes and 1,2-diaryldichloroethylenes

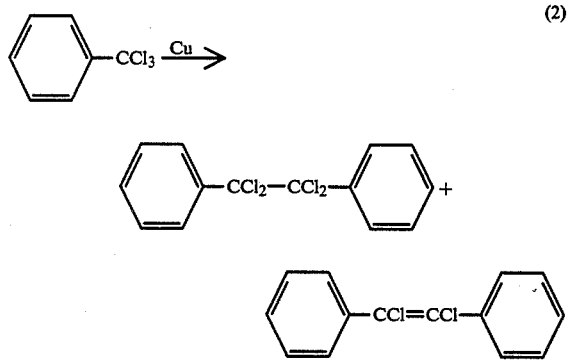  (2)

(T. L. Jacobs in Organic Reactions, Vol. V, John Wiley and Sons, Inc., New York, p. 43 (1949).

Krespan et al (J. Amer. Chem. Soc., Vol. 83, 3424 (1961) reported that the reaction of 1,1,1-trichloropolyfluoroalkanes with copper powder at 140°–200° C. give 1,2-dichloro-1,2-bis-(perfluoroalkyl)-ethylenes in 40–65% conversion

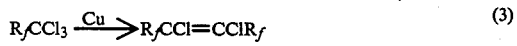  (3)

None of the above compounds contain a fluorine atom attached to the reactive center. When copper powder was added to Cl—CF$_2$—CFCl)$_2$Cl and the mixture heated to 250° C. for 3 days there was obtained a low conversion (less than 2%) to the coupled product Cl(CF$_2$CFCl)$_2$—(CFCl—CF$_2$)$_2$Cl.

It is accordingly an object of the present invention to provide a process for coupling of chloroperfluoroalkanes having a —CFCl$_2$ moiety.

This and other objects are realized in accordance with the invention pursuant to which such coupling is effected by heating the alkane at a temperature of about 150° to 260° C. in the presence of at least about 0.1 times the molar amount of each of copper and zinc at a mole ratio of copper:zinc from about 2:1 to 1:2.

Surprisingly, neither zinc nor copper alone produces comparable results of moderately high yields and conversions. While not wishing to be bound thereby, it is believed that the copper initially reacts to produce some cuprous chloride which in turn reacts with the zinc to form highly active metallic copper which thereafter makes the reaction proceed in high yield and conversion. Thus it is possible to start with cuprous chloride in place of copper per se, the copper per se being formed in situ. Preferably, however, the zinc and copper are utilized as metals of 10 micron particle size or smaller.

Advantageously the mole ratio of copper:zinc ranges from about 2:1 to 1:2, preferably from about 1:1 to 1:2 and each is present in at least about 0.1 times the molar amount of starting alkane, preferably 0.1 to 2 times the molar amount.

Advantageously the starting alkane is of the formula

Cl (CF$_2$—CFCl)$_n$Cl wherein n is 2 to 7 or an isomer thereof containing a CFCl$_2$ moiety. It may comprise a mixture of such alkanes, the coupled products varying accordingly. Thus, for example, from a starting material comprising a mixture of alkanes wherein n is 2 and 3 there are produced octanes, decanes and dodecanes.

Preferably, the temperature is from about 200° to 260° C., temperatures above 260° C. sometimes resulting in uncontrolled reaction. The reaction is almost complete in a few hours but the exact reaction time is determined by the temperature employed and the conversion desired.

The reaction may be conducted in the presence of a diluent but it is not necessary and would have to be removed.

Where necessary or desired for further use, the reaction product is subjected to distillation to separate unreacted starting material and relatively highly volatile by-products from coupled unsaturated material and coupled saturated material, and the coupled unsaturated material is halogenated, preferably chlorinated and/or fluorinated, thereby producing more of the desired product.

The invention will be further described in the following illustrative examples:

EXAMPLE 1

A mixture of isomers of C$_4$Cl$_4$F$_6$ (1368 g), zinc powder (260 g) and copper powder (127 g) were heated at 250° C. under nitrogen in a stirred autoclave at autogenous pressure. After 72 hours, GLC analysis showed 37% saturated "dimeric" and 7% saturated "trimeric" products, together with 10% unsaturated, coupled products. The mixture was centrifuged to remove the solids and the dark oil was flash distilled. The distillate was chlorinated at 100° C. for 2 days using a sunlamp. The crude oil was fractionally distilled to yield a volatile forerun and unchanged starting material. The residue was distilled under reduced pressure to obtain the coupled products. The total yield of coupled, useful products was 71% and the conversion was 72%.

Similarly, by varying the amount of copper and zinc per mole of $C_4Cl_4F_6$ isomers, the following results were obtained:

| Zinc Moles | Copper Moles | Temp °C. | Time Hours | Conversion % | Yield % Coupled Products |
|---|---|---|---|---|---|
| 0.16 | 0.16 | 250 | 72 | 13 | 85 |
| 0.33 | 0.33 | 260 | 72 | 28 | 82 |
| 0.33 | 0.16 | 260 | 72 | 25 | 84 |
| 0.16 | 0.33 | 260 | 72 | 20 | 75 |
| 0.33 | 0.33 | 260 | 90 | 31 | 81 |
| 0.66 | 0.44 | 250 | 96 | 42 | 79 |
| — | 0.16 | 250 | 72 | 1.5 | 38 |
| 0.16 | — | 210 | 24 | 0 | 0 |
| 0.33 | 0.16 | 235 | 36 | 28 | 89 |
| 0.56 | 0.38 | 240 | 24 | 57 | 83 |
| 0.42 | 0.29 | 240 | 6 | 21 | 75 |
| 0.42 | 0.29 | 240 | 12 | 36 | 75 |

EXAMPLE 2

A mixture of isomers of $C_4Cl_4F_6$ (608 g) and $C_6Cl_5F_9$ (1680 g) were stirred together with zinc powder (260 g) and copper powder (127 g) at 240° C. under nitrogen in an autoclave at autogenous pressure. After 74 hours GLC analysis showed a 70% yield of coupled products with a 44% conversion.

EXAMPLE 3

A mixture of isomers of $C_4Cl_4F_6$ (1523 g), zinc powder (256 g) and copper powder (124 g) were heated together in a stirred autoclave fitted with a water-cooled reflux condenser. The pressure in the system was regulated to maintain efficient reflux at a pot temperature of 215° C. After 44 hours, GLC analysis showed a 93% yield of coupled products with a 46% conversion.

Similarly, by varying the amounts of copper and zinc per mole of $C_4Cl_4F_6$ isomers, the following results were obtained:

| Zinc Moles | Copper Moles | Temp °C. | Time Hours | Conversion % | Yield % Coupled Products |
|---|---|---|---|---|---|
| 0.78 | 0.39 | 190 | 27 | 23 | 91 |
| 0.59 | 0.59 | 212 | 29 | 49 | 90 |
| 0.78 | 0.78 | 215 | 29 | 66 | 87 |

It will be understood that the specification and examples are illustrative but not limitative of the present invention and that other embodiments within the spirit and scope of the invention will suggest themselves to those skilled in the art.

What is claimed:

1. A process for the coupling of a chloroperfluoroalkane of the formula $$Cl(CF_2-CFCl)_nCl$$

in which n is 2 to 7, which comprises heating the alkane at a tempertature of about 150° to 260° C. in the presence of at least about 0.1 times the molar amount of each of copper and zinc at a mole ratio of copper: zinc from about 2:1 to 1:2.

2. A process according to claim 1, wherein the temperature is from about 200° to 260° C.

3. A process according to claim 1, wherein the mole ratio of copper:zinc is from about 1:1 to 1:2, and each is present in about 0.1 to 2 times the molar amount of the starting alkane.

4. A process according to claim 1, wherein the starting alkane being heated comprises a mixture of isomers.

5. A process according to claim 1, wherein the starting alkane comprises a mixture chlorofluorobutones and chlorofluorohexanes.

6. A process according to claim 1, wherein the reaction product is subjected to distillation to separate unreacted starting material and relatively highly volatile by-products from coupled unsaturated material and coupled saturated material, and the coupled unsaturated material is halogenated.

7. A process according to claim 6, wherein the coupled unsaturated material is chlorinated and/or fluorinated.

8. A process according to claim 1, wherein n is 2 or 3.

9. A process according to claim 1 wherein the reaction is conducted under reflux in the absence of a solvent.

* * * * *